United States Patent
Kadam et al.

(10) Patent No.: US 8,591,912 B1
(45) Date of Patent: Nov. 26, 2013

(54) ALGAE EXTRACTION PROCESS

(71) Applicants: Kiran L. Kadam, Ann Arbor, MI (US);
Brian Leslie Goodall, Spring, TX (US)

(72) Inventors: Kiran L. Kadam, Ann Arbor, MI (US);
Brian Leslie Goodall, Spring, TX (US)

(*) Notice: Subject to any disclaimer, the term of this patent is extended or adjusted under 35 U.S.C. 154(b) by 0 days.

(21) Appl. No.: 13/779,871

(22) Filed: Feb. 28, 2013

(51) Int. Cl.
*A61K 36/02* (2006.01)
*A61K 31/20* (2006.01)
*C11C 1/00* (2006.01)
*C11B 1/00* (2006.01)

(52) U.S. Cl.
USPC ......... 424/195.17; 554/20; 514/560; 435/271

(58) Field of Classification Search
None
See application file for complete search history.

(56) References Cited

U.S. PATENT DOCUMENTS

| | | | |
|---|---|---|---|
| 5,281,732 A | 1/1994 | Franke | |
| 6,258,964 B1 * | 7/2001 | Nakajima et al. | 554/12 |
| 7,192,731 B2 * | 3/2007 | Kanner et al. | 435/19 |
| 8,153,137 B2 | 4/2012 | Kale | |
| 2010/0261922 A1 * | 10/2010 | Fleischer et al. | 554/206 |
| 2010/0317088 A1 * | 12/2010 | Radaelli et al. | 435/259 |
| 2012/0238732 A1 | 9/2012 | Wang | |

FOREIGN PATENT DOCUMENTS

| | | |
|---|---|---|
| CN | 102277230 | 6/2010 |
| KR | 101115357 | 9/2010 |
| WO | WO 2008060571 A2 * | 5/2008 |
| WO | WO 2010039030 A1 * | 4/2010 |
| WO | WO 2010089063 A1 * | 8/2010 |
| WO | WO 2011159682 A1 * | 12/2011 |

OTHER PUBLICATIONS

Nagle et al. (1990) Applied Biochemistry and Biotechnology 24: 355-61.*
Halim et al. (2011) Bioresource Technology 102(1): 178-185.*
Mercer et al. (2011) Eur. J. Lipid Sci. Technol. 113, 539-547.*
Halim et al. (2012) Biotechnology Advances 30: 709-732.*

* cited by examiner

*Primary Examiner* — Chris R Tate
*Assistant Examiner* — Russell Fiebig
(74) *Attorney, Agent, or Firm* — Kohn & Associates PLLC

(57) ABSTRACT

A method of extracting oil from algae by drying algae paste to a predetermined moisture content, contacting the algae paste with a polar solvent to make an algae-solvent solution and extracting oils from the algae paste into a solvent-oil solution, and separating extracted algae from the solvent-oil solution. An oil of whole and unhydrolyzed phospholipids, whole and unhydrolyzed glycolipids, lysolipids, and carotenoids extracted by the above method. An omega-3 fatty acid of docosahexanoic acids (DHAs) and eicosapentaenoic acids (EPAs) extracted from the above method. Isolated nutraceutical grade and pharmaceutical grade oil derived from algae and being free of toxins extracted by the above method. Isolated oil derived from algae including at least one omega-3 fatty acid of DHA and EPA at least partially in the form of whole and unhydrolyzed phospholipids and whole and unhydrolyzed glycolipids extracted by the above method.

14 Claims, 1 Drawing Sheet

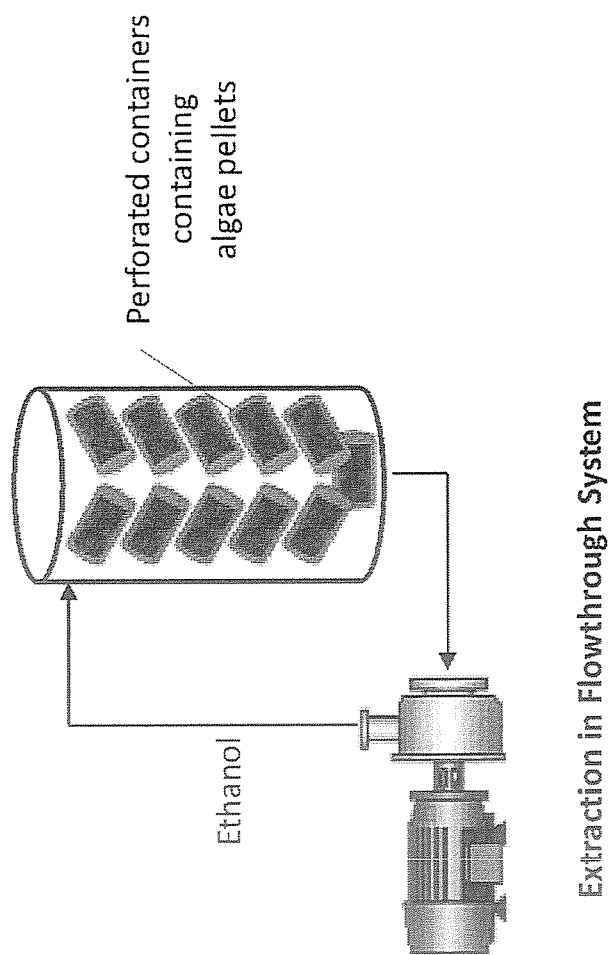

ALGAE EXTRACTION PROCESS

BACKGROUND OF THE INVENTION

1. Technical Field

The present invention relates to methods of extraction of oil from biomass, and in particular, algae. The present invention further relates to methods of extraction from algae biomass containing a controlled level of moisture.

2. Background Art

The mechanism of solvent extraction from oil-bearing biomass has been well studied, and engineers have applied leaching theory, diffusion theory, soaking theory, and viscous capillary flow to explain extraction kinetics and design efficient extractors (L. A. Johnson, 1997. "Theoretical, Comparative, and Historical Analyses of Alternative Technologies for Oilseeds Extraction", p. 4-47. In P. J. Wan and P. J. Wakelyn (ed.), Technology and solvents for extracting oilseeds and nonpetroleum oil. The American Oil Chemists Society, Champaign, Ill.). In commercial operations, most oilseeds undergo significant pre-extraction processing to improve extraction efficacy. For example, seeds are generally heated, cracked, and flaked, thereby rupturing cell walls and making oil more available to extraction solvents. Furthermore, flaking reduces the distance over which the oil must be transferred to dissolve in the solvent. Since the transfer mechanism is highly dependent on capillary flow, and to some extent on the viscosity of the solvent and miscella (oil-solvent mixture), feedstock preparation and solvent choice are large factors in extraction yields. In fact, flake thickness is often regarded as the most important factor in extraction efficiency, suggesting that feedstock preparation is a crucial part of the process that cannot be neglected when considering extracting lipids from microalgae (P. J. Wan and P. J. Wakelyn (ed.), Technology and solvents for extracting oilseeds and nonpetroleum oil. The American Oil Chemists Society, Champaign, Ill., 1997).

In reference to soybeans, Johnson (1997) notes that oil in unruptured cells diffuses out of the cell by osmosis, which is a very slow process and whose rate depends on the molecular size of the oil and solvent. Analogous considerations should be made for algae biomass: intact algae cells with durable cell walls represent a barrier to extraction of intracellular compounds, such as triglycerides, fatty acids and other lipids within the intact cell. Cell disruption by homogenization, sonication, high pressure, and pure solvents have all been investigated and reported to significantly influence the amount of recovered oil. Lipid solubility is a crucial factor in extraction procedures because success is predicated on finding a solvent system that will dissolve the lipids of interest while overcoming the interactions between lipids and their surroundings (S. J. Iverson et al., "Comparison of the Bligh and Dyer and Folch methods for total lipid determination in a broad range of marine tissue", Lipids 36 (11), (2001) 1283-1287). Generally, the solubility of pure lipids depends on their polarity and that of the solvent. Triglycerides are very soluble in non-polar solvents such as hexane, cyclohexane, and toluene, as well as slightly more polar solvents like chloroform (W. W. Christie (2003) Lipid analysis: isolation, separation, identification and structural analysis of lipids"). The solubility of triglycerides in polar solvents, such as alcohols, is very low. As alcohol chain-length increases and fatty acid chain length decreases, triglycerides become more soluble in alcohols; however, the surprising efficacy of ethanol in extracting algal lipids in the C16 to C22 chain length is clearly not obvious to someone ordinarily skilled in the art. In contrast to simple lipids, polar complex lipids have low solubility in hydrocarbon solvents, but can dissolve readily in chloroform, methanol, and ethanol (W. W. Christie (2003) Lipid analysis: isolation, separation, identification and structural analysis of lipids"). These observations teach that different solvents are needed to efficiently extract the different lipids within the algal biomass.

Recognizing the need to balance non-polar solvents capable of dissolving simple (neutral) lipids with polar solvents capable of extracting complex lipids, scientists and engineers have developed procedures using mixtures of solvents such as 2:1 blends of chloroform and methanol to quantitatively recover almost all major lipid classes from a variety of samples. These procedures, originally developed by Bligh and Dyer, Folch and others underlie all of the current knowledge regarding lipid content (and lipid extraction) in microalgae. These technologies are then applied to biomass that is pretreated (e.g. homogenization in a blender) as described above. These methods are unsuitable for commercial application due to the impracticality of using and recycling solvent mixtures, the toxicity of the preferred solvents (such as chloroform, hexane, and methanol) and their unacceptability in key applications such as nutraceuticals, pharmaceuticals and nutrition. These methods are unsuitable for extracting valuable oils such as omega-3 oils from phospholipids and glycolipids. These methods also use mechanical means requiring excessive energy (resulting in unfavorable energy balance and high costs plus degradation of the resulting algae fractions) or high temperatures that decrease the value of the products due to oxidation, isomerization, hydrolysis, degradation, or other pathways to decomposition.

There are several processes currently used that involve dry biomass or drying wet biomass to an extent. For example, U.S. Pat. No. 6,441,208 to Biil, et al. discloses a microbial polyunsaturated fatty acid (PUFA)-containing oil with a high triglyceride content (greater than 90%), and hence essentially devoid of polar lipids, and a high oxidative stability. In addition, a method is disclosed of the recovery of such oil from a microbial biomass derived from a pasteurized fermentation broth, wherein the microbial biomass is subjected to extrusion to form granular particles, dried and the oil then extracted from the dried granules using an appropriate solvent. The '208 patent forms granules out of dry biomass powder (the biomass can be algae). Solvent is then contacted with the granules, and the solvent can be ethanol or other alcohols to extract compounds/oils.

U.S. Pat. No. 7,868,195 to Fleischer, et al. discloses centrifuging a wet algal biomass to increase a solid content of the wet algal biomass to between approximately 10% and 40% to result in a centrifuged algal biomass, mixing the centrifuged algal biomass with an amphiphilic solvent to result in a mixture, heating the mixture to result in a dehydrated, defatted algal biomass, separating the amphiphilic solvent from the dehydrated, defatted algal biomass to result in amphiphilic solvent, water and lipids, evaporating the amphiphilic solvent from the water and the lipids, and separating the water from the lipids. The amphiphilic solvent may be selected from a group consisting of acetone, methanol, ethanol, isopropanol, butanone, dimethyl ether, and propionaldehyde. Other exemplary methods include filtering a wet algal biomass through a membrane to increase a solid content of the wet algal biomass to between approximately 10% and 40% to result in a filtered algal biomass. Separation can be performed by membrane filtration or centrifugation.

U.S. Pat. No. 8,153,137 to Kale discloses a method of isolating nutraceuticals products from algae. A method of isolating carotenoids and omega-3 rich oil from algae includes dewatering substantially intact algal cells to make an algal biomass and adding a first ethanol fraction to the algal biomass. The method also includes separating a first substantially solid biomass fraction from a first substantially liquid fraction comprising proteins and combining the first substantially solid biomass fraction with a second ethanol fraction. The method further includes separating a second substantially solid biomass fraction from a second substantially liquid fraction comprising polar lipids and combining the second substantially solid biomass fraction with a third ethanol solvent fraction. The method also includes separating a third substantially solid biomass fraction from a third substantially liquid fraction comprising neutral lipids, wherein the third substantially solid biomass fraction comprises carbohydrates and separating the neutral lipids into carotenoids and omega-3 rich oil. This is an energy intensive process due to the many step-wise separation steps required and is generally not a practical process. This process is a fractionation process to obtain proteins, polar lipids, carbohydrates, carotenoids, chlorophyll, and omega-3 fatty acids.

There remains a need for a method of extracting valuable algae oils from algae without causing damage to their structure, composition or commercial value (or that of the residual extracted algae meal) and without using solvents that are unacceptable in the above markets, since residual levels of said solvents diminish the value of the final products, and in many cases make them unacceptable in that market segment. There further remains a need for a method of extraction that is energy and cost efficient.

SUMMARY OF THE INVENTION

A method of extracting oil from algae, consisting essentially of the steps of drying algae paste to a predetermined moisture content, contacting the resulting algae paste with a polar solvent to make an algae-solvent solution and extracting oils from the algae paste into a solvent-oil solution, and separating extracted algae from the solvent-oil solution.

An oil such as phospholipids, whole and unhydrolyzed glycolipids, lysolipids, or carotenoids extracted by the above method.

An omega-3 fatty acid chosen from the group consisting of docosahexanoic acids (DHAs) and eicosapentaenoic acids (EPAs) extracted from the above method.

Isolated nutraceutical grade and pharmaceutical grade oil derived from algae and being free of toxins extracted by the above method.

Isolated oil derived from algae comprising at least one omega-3 fatty acid chosen from the group consisting of DHA and EPA at least partially in the form of whole and unhydrolyzed phospholipids and whole and unhydrolyzed glycolipids extracted by the above method.

DESCRIPTION OF THE DRAWINGS

Other advantages of the present invention are readily appreciated as the same becomes better understood by reference to the following detailed description when considered in connection with the accompanying drawings wherein:

FIG. 1 is a schematic of extraction in a flowthrough system.

DETAILED DESCRIPTION OF THE INVENTION

Most generally, the present invention is directed to a method of oil extraction from algae using a solvent extraction process. In contrast to many teachings in the prior art that microalgae must be extensively lysed or cracked by either chemical, enzymatic or energy intensive physical means, surprisingly it has been found that simply drying the microalgae to a moisture content of greater than 25%, preferably greater than 35% moisture and then extracting with alcohols, preferably ethanol, n-propanol or iso-propanol results in highly efficient extraction of the contained oil without any of the above, costly pre-treatments and furthermore the extracted oils are found to contain the valuable lipids in the form found in the biomass without degradation of any kind.

While the present invention is preferably practiced on "algae" or "microalgae", it should be understood that other forms of biomass can also be used.

"Polar" as used herein refers to a compound that has portions of negative and/or positive charges forming negative and/or positive poles. While a polar compound does not carry a net electric charge, the electrons are unequally shared between the nuclei. Water is considered a polar compound in the present invention.

"Oil" as used herein refers to any combination of fractionable lipid fractions of a biomass. "Lipid," "lipid fraction," or "lipid component" as used herein can include any hydrocarbon soluble in non-polar solvents and insoluble, or relatively insoluble, in water. The fractionable lipid fractions can include, but are not limited to, free fatty acids, waxes, sterols and sterol esters, triacylglycerols, diacylglycerides, monoacylglycerides, tocopherols, eicosanoids, glycoglycerolipids, glycosphingolipids, sphingolipids, and phospholipids. The lipid fractions can also comprise other liposoluble materials such as chlorophyll and other algal pigments, including, for example, antioxidants and carotenoids such as astaxanthins.

"Biomass" is used to refer to any living or recently dead biological cellular material derived from plants or animals. In certain embodiments, biomass can be selected from the group consisting of fungi, bacteria, yeast, mold, and microalgae. In other embodiments, the biomass can be agricultural products, such as corn stalks, straw, seed hulls, sugarcane leavings, bagasse, nutshells, and manure from cattle, poultry, and hogs, wood materials, such as wood or bark, sawdust, timber slash, and mill scrap, municipal waste, such as waste paper and yard clippings, or crops, such as poplars, willows, switchgrass, alfalfa, prairie bluestem, corn, and soybean. In certain embodiments, the biomass used with the invention is derived from plants.

Any biomass as defined herein can be used with the methods of the invention. In certain embodiments, the biomass is selected from the group consisting of fungi, bacteria, yeast, mold, and microalgae. The biomass can be naturally occurring, or it can be genetically modified to enhance lipid production. In a preferred embodiment, the biomass is microalgae. The present invention can be practiced with any microalgae. The microalgae can be grown in a closed system, such as a bioreactor, or it can be grown in open ponds. The microalgae can be grown with or without sunlight (autotrophically or heterotrophically) and with many varied carbon sources. The microalgae used with the invention can include any naturally occurring species or any genetically engineered microalgae. In particular, the microalgae can be genetically engineered to have improved lipid production characteristics, including but not limited to optimizing lipid yield per unit volume and/or per unit time, carbon chain length (e.g., for biodiesel production or for industrial applications requiring hydrocarbon feedstock), reducing the number of double or triple bonds, optionally to zero, removing or eliminating rings and cyclic structures, and increasing the hydrogen:carbon ratio of a particular species of lipid or of a population of distinct lipids. In addition, microalgae that naturally produce appropriate hydrocarbons can also be engineered to have even more desirable hydrocarbon outputs. The microalgae can be grown in freshwater, brackish water, brines, or saltwater. The microalgae used with the invention include any commercially available strain, any strain native to a particular region, or any proprietary strain. Additionally, the microalgae can be of any Division, Class, Order, Family, Genus, or Species, or any subsection thereof. Combinations of two or more microalgae also fall within the scope of the invention.

Microalgae can be harvested by any conventional means (including, but not limited to filtration, air flotation and centrifugation) and the algal paste generated by concentrating the harvested microalgae to the desired weight % of solids.

In certain embodiments, the microalgae used with the methods of the invention are members of one of the following divisions: Chlorophyta, Cyanophyta (Cyanobacteria), and Heterokontophyta. In certain embodiments, the microalgae used with the methods of the invention are members of one of the following classes: Bacillariophyceae, Eustigmatophyceae, and Chrysophyceae. In certain embodiments, the microalgae used with the methods of the invention are members of one of the following genera: *Nannochloropsis, Chlorella, Dunaliella, Scenedesmus, Selenastrum, Oscillatoria, Phormidium, Spirulina, Amphora,* and *Ochromonas*.

Non-limiting examples of microalgae species that can be used with the methods of the present invention include: *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella candida, Chlorella capsulate, Chlorella desiccate, Chlorella ellipsoidea, Chlorella emersonii, Chlorella fusca, Chlorella fusca* var. *vacuolata, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis, Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Effipsoidon* sp., *Euglena* spp., *Franceia* sp., *Fragilaria crotonensis, Fragilaria* sp., *Gleocapsa* sp., *Gloeothamnion* sp., *Haematococcus pluvialis, Hymenomonas* sp., *Isochrysis* aff. *galbana, Isochrysis galbana, Lepocinclis, Micractinium, Micractinium, Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrina, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricornutum, Phagus, Phormidium, Platymonas* sp., *Pleurochrysis carterae, Pleurochrysis dentate, Pleurochrysis* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocystisf, Tagetes erecta, Tagetes patula, Tetraedron, Tetraselmis* sp., *Tetraselmis suecica, Thalassiosira weissflogii,* and *Viridiella fridericiana*. Preferably, the microalgae are autotrophic.

In certain embodiments, the biomass can be wild type or genetically modified yeast. Non-limiting examples of yeast that can be used with the present invention include *Cryptococcus curvatus, Cryptococcus terricolus, Lipomyces starkeyi, Lipomyces lipofer, Endomycopsis vernalis, Rhodotorula glutinis, Rhodotorula gracilis, Candida* 107, *Saccharomyces paradoxus, Saccharomyces mikatae, Saccharomyces bayanus, Saccharomyces cerevisiae,* any *Cryptococcus, C. neoformans, C. bogoriensis, Yarrowia lipolytica, Apiotrichum curvatum, T. bombicola, T. apicola, T. petrophilum, C. tropicalis, C. lipolytica,* and *Candida albicans*.

In certain embodiments, the biomass can be a wild type or genetically modified fungus. Non-limiting examples of fungi that can be used with the present invention include *Mortierella, Mortierrla vinacea, Mortierella alpine, Pythium debaryanum, Mucor circinelloides, Aspergillus ochraceus, Aspergillus terreus, Pennicillium iilacinum, Hensenulo, Chaetomium, Cladosporium, Malbranchea, Rhizopus,* and *Pythium*.

In other embodiments, the biomass can be any bacteria that generate lipids, proteins, and carbohydrates, whether naturally or by genetic engineering. Non-limiting examples of bacteria that can be used with the present invention include *Escherichia coli, Acinetobacter* sp. any actinomycete, *Mycobacterium tuberculosis,* any streptomycete, *Acinetobacter calcoaceticus, P. aeruginosa, Pseudomonas* sp., *R. erythropolis, N. erthopolis, Mycobacterium* sp., B., *U. zeae, U. maydis, B. lichenformis, S. marcescens, P. fluorescens, B. subtilis, B. brevis, B. polmyma, C. lepus, N. erthropolis, T. thiooxidans, D. polymorphis, P. aeruginosa* and *Rhodococcus opacus*.

More specifically, the present invention provides for a method of extracting oil from algae, consisting essentially of the steps of drying algae paste to a predetermined moisture content, contacting the algae paste with a polar solvent to make an algae-solvent solution and extracting oils from the algae paste into a solvent-oil solution, and separating extracted algae from the solvent-oil solution. It is preferable that additional steps are not performed in this process to minimize cost and energy while obtaining desired products. In other words, it is this unique combination of steps that allows the particular products described below to be obtained.

Preferably, the algae paste is dried to a moisture content of between 15 and 75%, and more preferably, between 45 and 55%.

The algae paste can preferably be converted into particles with a predetermined moisture content such as, but not limited to, granules (spherical in shape), flakes (flat and disc-like in shape), or pellets (cylindrical in shape). The converting step can be performed in a single drying/granulating operation. The algae paste can be converted into flakes using a drum dryer, scraped surface dryer, or similar techniques, or preferably converted into granules or pellets using extrusion devices (a single extruder, a twin-screw extruder, a co-rotating extruder, a counter-rotating extruder, an extruder with steam injection, an extruder without steam injection) or an industrial expander. A Soxhlet process can also be used. The particles can preferably be a size of 0.2 mm to 2 mm in diameter and 0.5 to 5 mm in length, and other suitable sizes can be used. The particles allow for high porosity and extractability with sufficient size to permit facile separation of the extracted biomass from the solvent or oil in solvent solution.

Prior to converting the algae paste into particles, an additive can optionally be added to give the particles improved integrity and robustness. The additive can be, but is not limited to, bentonite, cellulose, diatomaceous earth, sawdust, kaolin, silica gel, super absorbent polymers, starch, CMC (carboxymethyl cellulose), PVDF (polyvinylidene fluoride), acacia gum (gum Arabic), dextrins, or combinations thereof. The additives preferably are acceptably utilized as components in animal and fish feed.

Also prior to the converting step, a front end step can be performed to remove the first extract (or miscella) that can remove most of the water. This allows for the rest of the extraction process to be essentially anhydrous, which is beneficial. This can be a dehydration step using liquid-liquid extraction rather than thermal dehydration, which can be detrimental.

The polar solvent that is contacted with the dried algae paste can be, but is not limited to, ethanol, n-propanol, isopropanol, butanol, acetone, or mixtures thereof. The polar solvent can also be an alcohol-water mixture.

The oil extracted preferably includes whole and unhydrolyzed phospholipids, whole and unhydrolyzed glycolipids, lysolipids, and carotenoids. The carotenoids can include astaxanthin and beta-carotene. Omega-3 fatty acids such as docosahexanoic acids (DHAs) and eicosapentaenoic acids (EPAs) can further be extracted from the oil. It should be understood that these acids are largely in the form of polar lipids (such as glycolipids) and not as free fatty acids. These oils can be recovered from the solvent-oil solution by any separation mechanisms known in the art.

The separating step to separate the extracted algae from the solvent-oil solution can be accomplished by any suitable mechanisms known in the art, such as, but not limited to, decantation, centrifugation, or filtration, with filtration or membrane filtration being preferred. A basket centrifuge, a continuous countercurrent extractor, of an immersion or a percolation type, etc. can be used. The most preferred separation method is through a wire mesh utilized in a shallow bed extractor. A primary purpose of making pellets or flakes is to minimize the amount of fines, which can plug the wedge-wire screen on the shallow bed extractor and slow down the drainage rate of solvent though the bed of material. The size of the pellet or flake can be adjusted so the percolation rate of solvent through the bed is slow enough so that the pellets are pretty much immersed in solvent but not so slow that the bed floods. A typical size of these pellets is in the range of ⅛" to ¼" in diameter, although smaller and larger sizes can be applied depending on the mesh size of the screen.

By performing the above method, a feed-grade meal can be produced that is highly digestible.

The present invention also provides for products extracted and recovered from the above method. For example, the present invention provides for an oil such as, but not limited to, whole and unhydrolyzed phospholipids, whole and unhydrolyzed glycolipids, lysolipids, or carotenoids. The carotenoids can be, but are not limited to, astaxanthin, and beta-carotene. Further, omega-3 fatty acids can be extracted (with fractional distillation methods) such as, but not limited to, docosahexanoic acids (DHAs) and eicosapentaenoic acids (EPAs). As above, these acids are largely in the form of polar lipids and not free fatty acids. These products are advantageous over prior art products because the oils are recovered whole and unhydrolyzed. In other words, the oils are not chemically or structurally modified unlike in other prior art processes.

The present invention also provides for isolated nutraceutical grade and pharmaceutical grade oil derived from algae and being free of toxins extracted by the above method. This process allows for the recovery of products that are not toxic to humans and animals and can be subsequently used in nutraceutical and pharmaceutical products.

The present invention also provides for isolated oil derived from algae including at least one omega-3 fatty acid such as, but not limited to, DHA or EPA at least partially in the form of whole and unhydrolyzed phospholipids and whole and unhydrolyzed glycolipids extracted by the above method. The oil isolated by this process is unexpectedly high in polar lipids such as phospholipids and glycolipids. It is known that krill oil, by virtue of the contained phospholipids (a polar lipid), has higher bioavailability in mammals than does fish oil, which comprises almost exclusively neutral lipids (triglycerides). (Jan Philipp Schuchardt et al., Lipids in Health and Disease 2011, 10:145). Remarkably the oils extracted from *Nannochloropsis* using the inventive methods showed bioavailability to mammals that surpassed even krill oil. While not wishing to be bound by theory, this important and surprising result can be attributed to the extremely high level of polar lipids contained suggesting that both phospholipids and glycolipids show high mammalian bioavailability.

The present invention provides several advantages over the processes of the prior art. The finding that microalgae can be efficiently extracted without any of the expensive, energy-intensive pre-treatment steps of the prior art is surprising and non-obvious to someone ordinarily skilled in the art. Also, using ethanol azeotropes with water rather than pure (100%) ethanol is similarly surprising and non-obvious to someone ordinarily skilled in the art.

Surprisingly, we have found conditions in which a simple solvent (preferably ethanol) can be used as the single solvent to extract all, or essentially all, the lipids in algal biomass—ranging from neutral lipids such as triglycerides to polar lipids such as phospho- and glycolipids. In contrast the surprising discovery of conditions and technology in which algal biomass, with little or no pre-treatment can be effectively extracted with a single solvent that is acceptable for valuable markets such as nutraceuticals, pharmaceuticals and nutrition is unexpected. Also surprising is the fact that ethanol/water azeotrope mixtures can be conveniently utilized. The use of azeotropes lowers the energy and recycling costs of the ethanol solvent dramatically, and azeotrope formation is inevitable since the algal biomass suitable for extraction using this process typically contains high levels of water.

The invention is further described in detail by reference to the following experimental examples. These examples are provided for the purpose of illustration only, and are not intended to be limiting unless otherwise specified. Thus, the invention should in no way be construed as being limited to the following examples, but rather, should be construed to encompass any and all variations which become evident as a result of the teaching provided herein.

EXAMPLE 1

Algae (*Nannochloropsis*) pellets containing about 50% solids (approximately 50% moisture were prepared. The weight of a blank thimble filter (22×90 mm) (Kimble-Chase, USA) and a blank 250 mL Erlenmeyer flask were weighed. After placing 10 g of algae pellets into thimble, about 100 mL of denatured ethanol (200% proof) is poured into the 250 mL Erlenmeyer extraction flask as an extraction solvent and placed on the electrical hot plate. A magnetic stir bar was placed inside the flask for continuous mixing. After this, the thimble containing the sample was placed into the extraction chamber. Lastly, the condenser was placed on top of the extraction flask and all these parts were fixed vertically. The extraction was carried out for three hours at 80-82° C. The extraction process was repeated three times and an average extraction yield was calculated. After the extraction process, the weight of thimble containing sample and the weight of 250 mL Erlenmeyer flask containing solvent and extracted crude algae oil were determined. Finally the solvent (ethanol) was removed using high-vacuum distillation process. The extracted oil was calculated as percentage of starting material. The extracted oil was stored in a refrigerator at the temperature <20° C. until analyzed by GC-FID and GCMS after the extraction process.

Results

Lipid Characterization

The main aim of the lipid characterization is to identify and quantify the fatty acid methyl esters (FAMEs) derived from mono-, di- and triacylglycerides. An approximate identification by alkyl chain length can be made using the retention times compared to standards by chromatographic analysis using GC with a flame ionization detector (FID). In the first step, triacylglycerides (TAGs) are extracted from a dry sample using the Soxhlet method. In the second step, the extracted TAGs are transesterified to FAMEs. The FAMEs are dissolved in a known quantity of heptane then quantified by GC-FID.

Sample Preparation for GC-FID Analysis

Approximately 100 mg of algal lipid was added to a small Teflon capped vial (40 mL) containing 10 mL methanol. Next, 0.8 mL of 5% acetyl chloride in methanol was added to the vial. The vial was tightly capped and heated in a water bath at 80-85° C. for 1 hour. After cooling, the sample was diluted to ~10,000 ppm concentration with heptane. The heptane was taken up in ~2 mL of HPLC vial and analyzed by GC-FID. Table 1 shows the oil yield, lipid profile results. The average extent of lipid extraction using Soxhlet process was about 42.8% (Table 1), this lipid yield pattern correlates with the results from different replicates. Interestingly, the lipid yield shows a maximum for eicosapentaenoic acid (EPA) in the oil.

TABLE 1

Algae oil yield and fatty acid profile

| Extraction condition | Soxhlet extraction |
|---|---|
| Oil yield (%) | 42.8 |

Fatty Acid Profile

| | | % OF FATTY ACIDS IN THE OIL (w/w %) | % OF TOTAL FATTY ACIDS (w/w %) |
|---|---|---|---|
| Fatty | C14:0 Myristic | 0.91 | 3.00 |
| Acid | C14:1 Myristoleic | 0.38 | 1.25 |
| Methyl | C16:0 Palmitic | 3.44 | 11.31 |
| Esters | C16:1n7 Palmitoleic | 5.79 | 19.05 |
| (FAME) | C16:2 hexadecadienoic | 0.56 | 1.84 |
| | C18:0 Stearic | 0.06 | 0.21 |
| | C18:1-Oleic | 0.78 | 2.57 |
| | C18:1-Vaccenic | 0.13 | 0.43 |
| | C18:2 Linoleic | 0.74 | 2.43 |
| | C18:3 Linolenic | 0.07 | 0.22 |
| | C20:0 Arachidic | 0.46 | 1.52 |
| | C20:1 Eicosenoic | 0.00 | 0.00 |
| | C20:2n6 Eicosadienoic | 0.16 | 0.54 |
| | C20:3n6 Homogamma Linolenic | 0.00 | 0.00 |
| | C20:4n6 Arachidonic | 1.86 | 6.11 |
| | C20:3n3 Eicosatrienoic | 0.04 | 0.15 |
| | C20:4n3 Eicosatetraenoic | 0.00 | 0.00 |
| | C20:5n3 Eicosapentaenoic | 12.87 | 42.35 |
| | C22:0 Behenic | 0.09 | 0.29 |
| | C24 Lignoceric | 0.00 | 0.00 |
| | C24:1 Nervonic | 0.00 | 0.00 |
| | C22:4n6 Docosatetraenoic | 0.00 | 0.00 |
| | C22:5n6 Docosapentaenoic | 0.21 | 0.68 |
| | Other | 1.85 | 6.05 |
| | Total FAME (%) in oil | 30.40 | 100.00 |

EXAMPLE 2

The proposed wet extraction method was compared with dry extraction using *Scenedesmus* sp. The wet extraction experiment was conducted in a manner similar to EXAMPLE 1 and the dry extraction was using a Soxhlet apparatus. The results are as follows. It is clear that the proposed wet extraction method is superior to dry extraction. Thus, drying algae to very low moisture is detrimental. While not being bound by theory, this could be explained by the fact that when dried the pretreated algae structure changes probably due to collapsing the matrix thereby limiting solvent access. This is somewhat reminiscent of cellulosic biomass, which also performs poorly in enzymatic hydrolysis if first dried and then pretreated.

TABLE 2

Algae oil yields for dry vs. wet extraction

| Extraction method | Oil yield, wt % dry algae | FAME yield, wt % dry algae |
|---|---|---|
| Dry Soxhlet extraction | 1.0 | ND* |
| Wet extraction | 21.9 | 11.3 |

*ND: not determined

EXAMPLE 3

This example shows reduction to practice using a flowthrough system. Schematic of the flowthrough system is depicted in FIG. 1. This is a novel way of processing as such besides being an example.

Nannochloropsis paste at 25% solids was extruded to make pellets, which were then dried in an oven to achieve about 50% solids content. These pellets were loaded into small perforated containers that were placed in a reactor. Ethanol was heated to about 70° C. and was circulated through the reactor for certain duration. The miscella, i.e., ethanol and oil mixture was collected and distilled to yield oil.

Benchtop Extractions

Starting material was *Nannochloropsis* sp. pellets at 50% solids: about 60 g on dry basis. Container shape: egg-shaped.

Diameter of containers: 1" at the broadest section.
Solvent-to-feed ratio (dry basis): 20.
Duration: 2 hours.

The results are shown in TABLE 3. High yields of EPA were reproducibly demonstrated. EPA thus recovered has been shown to have high bioavailability.

TABLE 3

Results of benchtop extractions

| Run | Oil yield, wt % dry algae | FAME yield, wt % dry algae | EPA yield, wt % dry algae |
|---|---|---|---|
| 1 | 49.5 | 14.1 | 5.6 |
| 2 | 48.8 | 14.7 | 6.7 |
| 3 | 50.0 | 14.8 | 6.9 |
| average | 49.4 | 14.5 | 6.4 |
| std dev | 0.6 | 0.3 | 0.7 |

Pilot-Scale Extractions

Starting material was *Nannochloropsis* sp. pellets at 46.7% solids (53.3% moisture): about 2.5 kg on dry basis. Container shape: cylindrical.

Diameter and height of containers: 5" and 2", respectively.
Solvent-to-feed ratio (dry basis): 6.
Duration: 4 hours.

The oil yield was 40.0 wt % of dry algae, which is lower than that at the bench scale. This can be explained by mass transfer limitations: as the containers are larger the distance ethanol has to travel is longer. This was corroborated by observing pellets in container interiors that still had some green color indicating less efficient contact with the solvent. Higher yields can be obtained by increasing the turbulence thereby reducing mass transfer resistance and with a higher solvent-to-feed ratio.

EXAMPLE 4

This example shows reduction to practice using a continuous countercurrent system.

Starting material was *Nannochloropsis* sp. granules at 47.8% solids (52.8% moisture): about 65 kg on dry basis.
Solvent-to-feed ratio (dry basis): 8.
Duration: 4 hours.
Continuous countercurrent system: similar to that used in soybean extraction.

The process was successfully reduced to practice and operationally demonstrated in the continuous countercurrent equipment at pilot demonstration scale. An oil yield on dry algae of 34.4% was observed. Again, higher yields can be obtained by optimizing process parameters such as solvent-to-feed ratio, temperature, time and particle size. This example illustrates how the process can be mechanically implemented at commercial scale.

Throughout this application, various publications, including United States patents, are referenced by author and year and patents by number. Full citations for the publications are listed below. The disclosures of these publications and patents in their entireties are hereby incorporated by reference into this application in order to more fully describe the state of the art to which this invention pertains.

The invention has been described in an illustrative manner, and it is to be understood that the terminology, which has been used is intended to be in the nature of words of description rather than of limitation.

Obviously, many modifications and variations of the present invention are possible in light of the above teachings. It is, therefore, to be understood that within the scope of the appended claims, the invention can be practiced otherwise than as specifically described.

What is claimed is:

1. A method of extracting oil from algae and microalgae consisting of the steps of:
   drying algae paste to moisture content of between 45 and 55%;
   contacting the algae paste with a polar solvent for a sufficient time to form an algae-solvent solution containing extract oil;
   separating the algae from the algae-solvent solution to form a solvent-oil solution; and
   recovering the oil from the solvent-oil solution.

2. The method of claim 1, wherein said drying step is further defined as drying algae paste and converting the algae paste into particles with a moisture content of between 45 and 55%.

3. The method of claim 2, wherein the particles are a size of 0.2 mm to 2 mm in diameter and 0.5 to 5 mm in length.

4. The method of claim 2, wherein the particles are chosen from the group consisting of granules, flakes, and pellets.

5. The method of claim 1, wherein the algae are autotrophic.

6. The method of claim 4, wherein said converting step is performed in a single drying operation.

7. The method of claim 1, wherein the polar solvent is chosen from the group consisting of ethanol, n-propanol, iso-propanol, butanol, acetone, and mixtures thereof.

8. The method of claim 1, wherein the polar solvent is an alcohol-water mixture.

9. The method of claim 1, wherein the oil includes whole and unhydrolyzed phospholipids, whole and unhydrolyzed glycolipids, lysolipids, and carotenoids.

10. The method of claim 9, wherein the carotenoids are chosen from the group consisting of astaxanthin and beta-carotene.

11. The method of claim 1, wherein the microalgae is chosen from the group consisting of *Achnanthes orientalis, Agmenellum* spp., *Amphiprora hyaline, Amphora coffeiformis, Amphora coffeiformis* var. *linea, Amphora coffeiformis* var. *punctata, Amphora coffeiformis* var. *taylori, Amphora coffeiformis* var. *tenuis, Amphora delicatissima, Amphora delicatissima* var. *capitata, Amphora* sp., *Anabaena, Ankistrodesmus, Ankistrodesmus falcatus, Boekelovia hooglandii, Borodinella* sp., *Botryococcus braunii, Botryococcus sudeticus, Bracteococcus minor, Bracteococcus medionucleatus, Carteria, Chaetoceros gracilis, Chaetoceros muelleri, Chaetoceros muelleri* var. *subsalsum, Chaetoceros* sp., *Chlamydomas perigranulata, Chlorella anitrata, Chlorella antarctica, Chlorella aureoviridis, Chlorella candida, Chlorella capsulate, Chlorella desiccate, Chlorella ellipsoidea, Chlorella emersonii, Chlorella fusca, Chlorella fusca* var. *vacuolata, Chlorella glucotropha, Chlorella infusionum, Chlorella infusionum* var. *actophila, Chlorella infusionum* var. *auxenophila, Chlorella kessleri, Chlorella lobophora, Chlorella luteoviridis, Chlorella luteoviridis* var. *aureoviridis,*

*Chlorella luteoviridis* var. *lutescens, Chlorella miniata, Chlorella minutissima, Chlorella mutabilis, Chlorella nocturna, Chlorella ovalis, Chlorella parva, Chlorella photophila, Chlorella pringsheimii, Chlorella protothecoides, Chlorella protothecoides* var. *acidicola, Chlorella regularis, Chlorella regularis* var. *minima, Chlorella regularis* var. *umbricata, Chlorella reisiglii, Chlorella saccharophila, Chlorella saccharophila* var. *ellipsoidea, Chlorella salina, Chlorella simplex, Chlorella sorokiniana, Chlorella* sp., *Chlorella sphaerica, Chlorella stigmatophora, Chlorella vanniellii, Chlorella vulgaris, Chlorella vulgaris* fo. *tertia, Chlorella vulgaris* var. *autotrophica, Chlorella vulgaris* var. *viridis, Chlorella vulgaris* var. *vulgaris, Chlorella vulgaris* var. *vulgaris* fo. *tertia, Chlorella vulgaris* var. *vulgaris* fo. *viridis, Chlorella xanthella, Chlorella zofingiensis, Chlorella trebouxioides, Chlorella vulgaris, Chlorococcum infusionum, Chlorococcum* sp., *Chlorogonium, Chroomonas* sp., *Chrysosphaera* sp., *Cricosphaera* sp., *Crypthecodinium cohnii, Cryptomonas* sp., *Cyclotella cryptica, Cyclotella meneghiniana, Cyclotella* sp., *Dunaliella* sp., *Dunaliella bardawil, Dunaliella bioculata, Dunaliella granulate, Dunaliella maritime, Dunaliella minuta, Dunaliella parva, Dunaliella peircei, Dunaliella primolecta, Dunaliella salina, Dunaliella terricola, Dunaliella tertiolecta, Dunaliella viridis, Dunaliella tertiolecta, Eremosphaera viridis, Eremosphaera* sp., *Ellipsoidon* sp., *Euglena* spp., *Franceia* sp., *Fragilaria crotonensis, Fragilaria* sp., *Gleocapsa* sp., *Gloeothamnion* sp., *Haematococcus pluvialis, Hymenomonas* sp., *Isochrysis* aff. *galbana, Isochrysis galbana, Lepocinclis, Micractinium, Micractinium, Monoraphidium minutum, Monoraphidium* sp., *Nannochloris* sp., *Nannochloropsis salina, Nannochloropsis* sp., *Navicula acceptata, Navicula biskanterae, Navicula pseudotenelloides, Navicula pelliculosa, Navicula saprophila, Navicula* sp., *Nephrochloris* sp., *Nephroselmis* sp., *Nitschia communis, Nitzschia alexandrina, Nitzschia closterium, Nitzschia communis, Nitzschia dissipata, Nitzschia frustulum, Nitzschia hantzschiana, Nitzschia inconspicua, Nitzschia intermedia, Nitzschia microcephala, Nitzschia pusilla, Nitzschia pusilla elliptica, Nitzschia pusilla monoensis, Nitzschia quadrangular, Nitzschia* sp., *Ochromonas* sp., *Oocystis parva, Oocystis pusilla, Oocystis* sp., *Oscillatoria limnetica, Oscillatoria* sp., *Oscillatoria subbrevis, Parachlorella kessleri, Pascheria acidophila, Pavlova* sp., *Phaeodactylum tricornutum, Phagus, Phormidium, Platymonas* sp., *Pleurochrysis carterae, Pleurochrysis dentate, Pleurochrysis* sp., *Prototheca wickerhamii, Prototheca stagnora, Prototheca portoricensis, Prototheca moriformis, Prototheca zopfii, Pseudochlorella aquatica, Pyramimonas* sp., *Pyrobotrys, Rhodococcus opacus, Sarcinoid chrysophyte, Scenedesmus armatus, Schizochytrium, Spirogyra, Spirulina platensis, Stichococcus* sp., *Synechococcus* sp., *Synechocystisf, Tagetes erecta, Tagetes patula, Tetraedron, Tetraselmis* sp., *Tetraselmis suecica, Thalassiosira weissflogii,* and *Viridiella fridericiana.*

12. A method of extracting oil from algae and microalgae consisting of the steps of:
drying algae paste to moisture content of between 45 and 55%;
contacting the algae paste with a polar solvent for a sufficient time to form an algae-solvent solution containing extract oil;
separating the algae from the algae-solvent solution to form a solvent-oil solution;
recovering the oil from the solvent-oil solution; and
extracting omega-3 fatty acids chosen from the group consisting of docosahexanoic acid (DHA) and eicosapentaenoic acid (EPA) from the recovered oil.

13. A method of extracting oil from algae and microalgae consisting of the steps of:
adding an additive to algae paste;
drying the algae paste to moisture content of between 45 and 55%;
contacting the algae paste with a polar solvent for a sufficient time to form an algae-solvent solution containing extract oil;
separating the algae from the algae-solvent solution to form a solvent-oil solution; and
recovering the oil from the solvent-oil solution.

14. The method of claim 13, wherein the additive is chosen from the group consisting of bentonite, cellulose, diatomaceous earth, sawdust, kaolin, silica gel, super absorbent polymers, starch, CMC (carboxymethyl cellulose), PVDF (polyvinylidene fluoride), acacia gum (gum Arabic), dextrins, and combinations thereof.

\* \* \* \* \*